(12) United States Patent
Sugimoto et al.

(10) Patent No.: US 6,670,312 B2
(45) Date of Patent: Dec. 30, 2003

(54) COMPOSITION FOR REMOVAL OF CALCIUM OR MAGNESIUM COMPOUNDS FROM AN ARTICLE

(76) Inventors: Takeshi Sugimoto, 29-2, Nonoue 2-chome, Habikino-shi, Osaka 583-0871 (JP); Jiro Sakurai, 10-23, Sagisu 2-chome, Fukushima-ku, Osaka-shi, Osaka 553-0002 (JP)

( * ) Notice: Subject to any disclaimer, the term of this patent is extended or adjusted under 35 U.S.C. 154(b) by 1 day.

(21) Appl. No.: 09/733,101

(22) Filed: Dec. 8, 2000

(65) Prior Publication Data

US 2003/0096718 A1 May 22, 2003

(51) Int. Cl.$^7$ ................................................ C11D 17/00
(52) U.S. Cl. ..................... 510/109; 520/116; 520/117; 424/48; 424/49; 424/52; 424/88; 424/435; 424/440
(58) Field of Search ................... 510/109, 116, 510/117; 424/49, 48, 435, 440, 52, 88

(56) References Cited

U.S. PATENT DOCUMENTS

| | | | |
|---|---|---|---|
| 5,686,399 A | * 11/1997 | Bianchetti et al. | 510/191 |
| 6,008,171 A | * 12/1999 | Hughes et al. | 510/117 |
| 6,193,958 B1 | * 2/2001 | Edwards et al. | 424/49 |

FOREIGN PATENT DOCUMENTS

| | | |
|---|---|---|
| EP | WO95-21229 | 8/1995 |
| EP | WO96-19554 | 6/1996 |
| EP | WO97-02011 | 1/1997 |
| JP | 53-046302 | 4/1978 |
| JP | 59-020479 | 2/1984 |
| JP | 61-207500 | 9/1986 |
| JP | 71-57799 | 6/1995 |
| JP | 09-110664 | 4/1997 |
| JP | 2000-64069 | 2/2000 |

OTHER PUBLICATIONS

Examination Certified Report of Nongovernment Developed Technique In–vehicle type Chemicals & Systems Cleaning Method (CSC Method) published on Jul. 4, 1995, by Japan Sewage Works Agency.
Environment Newspaper ( p. 12 published on Jul. 2, 1997).

* cited by examiner

*Primary Examiner*—Necholus Ogden
(74) *Attorney, Agent, or Firm*—Rader, Fishman & Grauer PLLC

(57) ABSTRACT

A removing agent comprising a composition containing at least a hydroxycarboxylic acid and a sulfamic acid, said agent being adapted for use in removing calcium compounds, magnesium compounds and organic substances deposited on the dentures, or those on the inner surface of drainpipes for dental units and toilets, drainpipes in operating rooms and supply rooms of hospitals, and drainpipes in transportation means such as trains, vessels and aircraft, and also for use in removing filthy adhesives in various apparatus in the field of chemical industry associated with calcium, power generator equipment, heat exchangers, etc.

3 Claims, No Drawings

COMPOSITION FOR REMOVAL OF CALCIUM OR MAGNESIUM COMPOUNDS FROM AN ARTICLE

FIELD OF THE INVENTION

The present invention relates to agents capable of removing deposits or accumulations mainly containing calcium compounds and associated other mineralized compounds by dissolving.

BACKGROUND ART

Dental caries is thought attributable to *Streptococcus mutans* growing on food particles remaining in the oral cavity after meals and consequently producing acids, which dissolve the enamel surface of teeth. On the other hand, the remaining food particles decomposed by oral microorganisms which predominantly include *Streptococcus mutans* form dental plaque, which adheres to the surfaces of teeth and is converted into dental calculus with time.

Dental calculus consists mainly of inorganic mineralized salts contained in saliva and deposited on the surfaces of teeth, and of organic substances derived from saliva, bacteria and food particles. Dental calculus contains 82.9% (by weight, the same as hereinafter) of inorganic substances including 30.72% of calcium, 16.85% of phosphorus, 1.044% of magnesium, 0.0196% of iron and 1.393% of carbonic acid. The calculus contains 8.34% of proteins (including keratins, mucins and nucleoproteins) and 2.7% of fats. The calculus also contains trace amounts of metals such as; copper, silver, sodium, tin, zinc, aluminum, barium, strontium and chromium, according to Encyclopaedia Chimica (Kyoritsu Shuppan Co., Ltd., Japan). The main component of the dental calculus is calcium phosphate of apatite-type structure as is found in those of teeth and bones.

The mechanism of dental calculus formation is 1) the remaining food particles involved by oral microorganisms and 2) consequently deposited calcified mineral compounds from saliva. Dental calculus also contains magnesium compounds in amounts considerably smaller than those of calcium compounds.

"Dental spittoon" and a drainpipe connected thereto in the dental unit are used for a long period. Deposits of calcium and magnesium compounds and accumulation of non-calcified organic materials, which are generally referred to "scale", are adhered on surfaces of the drainpipe. It needs common practice to periodically clean the pipe with chemical agents; hydrochloric acid, sulfuric acid or strong acids, or caustic soda or like strong alkali or with a chlorine compounds, to flow into the pipe and to exclude the deposit or accumulation for decomposition.

For removing the scales with such chemicals, it not only deteriorates the drainpipe but also entails the problem that the waste water resulting from cleaning gives rise to environmental pollution. Furthermore, some chemicals used in combination are likely to evolve noxious chlorine gas.

Dental calculus is formed also on dentures surface through the same mechanism as described above. Removing calculus from the denture is the same manner as tooth brushing, using an abrasive material in the past as mechanically scrubbing off the calculus compounds. It is recently used in general practice the immersed denture in a cleaning solution, then thoroughly wash the denture with water and set the denture in the oral cavity. However, the denture cleaning agent could exclude lipids and proteins and has no or little effect to remove calcium compounds.

The conventional denture cleaning agent is adapted to exhibit cleaning ability by the combination of the bleaching effect of oxidizer, cleaning effect of surfactant, substrate decomposing effect of enzyme, cleaning and decomposing effect of alkali, cleaning assisting effect of chelating agent, stirring effect due to bubbling, etc. The oxidizer having a bleaching effect or the alkali serving as a cleaning agent, if used for long times, showed the occurrence of discoloring and deteriorating the polymethyl methacrylate resin and ceramic materials which are usually used as dental materials.

Since urine contains high amounts of calculus consisting mainly of inorganic compounds, such as calcium oxalate, the toilet bowl for use in daily and the drainpipe or the like connected thereto have the problem of calcium deposition on the inner wall of the pipe during a long period of use as seen the same in the drainpipe of the dental equipment.

An object of the present invention is to provide an agent for effectively removing deposits comprising substances discharged from the living body, especially deposits containing calcium and magnesium compounds.

The removing agent of the present invention is useful for cleaning dentures and also suitable for use in dental spittoon and drainpipes connected thereto, toilet devices and drainpipes connected thereto, and various drainpipes installed in the transportation means such as trains, vessels and aircraft, i.e., for uses involving the necessity of removing scale containing calcium compounds or magnesium compounds and deposited on inside of pipe walls.

SUMMARY OF THE INVENTION

The present invention provides an agent for removing calcium compounds and magnesium compounds, the agent being a composition comprising at least a hydroxycarboxylic acid and a sulfamic acid.

The agent of the invention for removing calcium compounds and magnesium compounds comprises a base composition containing at least a hydroxycarboxylic acid and a sulfamic acid and is prepared by mixing 5 to 100 parts by weight of a binder with 100 parts by weight of the base composition, and shaping the resulting mixture.

The hydroxycarboxylic acid to be used is, for example, at least one acid selected from the group consisting of glycolic acid, malic acid, lactic acid, tartaric acid, citric acid, hydroacrylic acid, alpha-hydroxybutyric acid, glyceric acid, tartronic acid, salicylic acid, m-hydroxybenzoic acid, p-hydroxybenzoic acid, gallic acid, mandelic acid and tropic acid.

The sulfamic acid to be used is, for example, amidosulfamic acid.

DETAILED DESCRIPTION OF THE INVENTION

A detailed description is stated below of the removing agent of the invention containing at least a hydroxycarboxylic acid and a sulfamic acid.

The term "hyroxycarboxylic acid" refers to acids including an alcoholic hydroxyl group and a carboxyl group in the molecule, such as aliphatic carboxylic acids including glycolic acid, malic acid, lactic acid, tartaric acid, citric acid, hydroacrylic acid, alpha-hydroxybutyric acid, glyceric acid and tartronic acid; and aromatic carboxylic acids including salicylic acid, m-hydroxybenzoic acid, p-hydroxybenzoic acid, gallic acid, mandelic acid and tropic acid. The acid used is not limited to these examples.

These carboxylic acids can be used singly, or at least two of them are usable when so desired.

Incidentally, the hydroxycarboxylic acid to be used can be any of levorotatory, dextrorotatory and racemic compounds with respect to the optical activity thereof. Levorotatory hydroxycarboxylic acids are naturally available and are therefore more preferable.

The sulfamic acid used is, for example, amidosulfamic acid. The N-alkyl and N-aryl derivatives of the amidosulfamic acid, which are highly soluble in water, are desirable to use. Such sulfamic acids are usable also singly, or at least two of them are usable when so desired.

The acids to be used in the present invention are those safe to use for a long period of time, preferably those which are solid at room temperature, and more preferably those resembling naturally productive acids in chemical structure and highly biodegradable.

The hydroxycarboxylic acid and the sulfamic acid are used preferably in a ratio by weight of 1:9 to 9:1, and more preferably 1:9 to 7:3.

The removing agent of the present invention can be used in the form of an aqueous solution or a powder, whereas when shaped into suitable forms of various sizes, the agent is adjustable in the dissolving-out concentration of the effective component and life.

The agent can be prepared in the shaped forms by mixing a powder of hydroxycarboxylic acid with a powder of sulfamic acid to obtain a basic composition, mixing 5 to 100 parts by weight of a binder powder with 100 parts by weight of the basic composition substantially uniformly, and shapes for the mixture as desired by a tableting machine.

Examples of binders usable are carboxymethylcellulose (CMC), sodium carboxymethylcellulose (CMC-Na), polyvinyl pyrrolidone (PVP), hydroxypropyl cellulose (HPC), hydroxypropyl methylcellulose (HPMC), methylcellulose (MC), hydroxypropyl starch (HPS), and similar carbohydrates or organic polysaccharide, although not limitative. These binders have activity to retard the dissolving of hydroxycarboxylic acid and sulfamic acid in water, such that the time taken for these acids to dissolve in water can be controlled as desired by varying the amount of binder to be used.

It is desirable to use the basic composition in the form of a powder or aqueous solution without the binder when it is required to produce an immediate effect on the substances to be removed (calcium compounds and/or magnesium compounds).

On the other hand, it is desired to shape the agent in the form of blocks and masses if these substances are to be dissolved slowly over a considerable period of time or to permit the agent as shaped to retain its efficacy for a predetermined period of time. For example, in the case where the agent is shaped into pills, use of a larger number of smaller pills results in a larger area of contact with water, produces a greater efficacy but entails a shorter service life than the use of a smaller number of larger pills if the same amount of the agent is used. Thus, the form of the agent and the size of the agent as shaped are determined suitably in accordance with the purpose of use.

The removing agent of the present invention can be used in combination with the components of conventional cleaning agents, such as oxidizer, surfactant, enzyme, chelating agent, etc. when so required.

The present invention is described below with reference to specific examples.

Preparation of Samples

INVENTION EXAMPLE 1

A 10 g of L-malic acid and 10 g of citric acid as hydroxycarboxylic acids and 5 g of amidosulfamic acid as a sulfamic acid were dissolved in 500 ml of distilled water to obtain a sample of the invention.

INVENTION EXAMPLE 2

A 100 g of L-malic acid and 50 g of citric acid as hydroxycarboxylic acids, 10 g of amidosulfamic acid as a sulfamic acid and 18 g of carboxymethylcellulose as a binder were thoroughly mixed together and made into tablets with a diameter of 5 mm to obtain a sample of the invention.

COMPARATIVE EXAMPLE 1

A commercially available cleaning agent for dentures was prepared as the sample of Comparative Example 1, the agent comprising 20 wt. % of potassium monosulfate, 40 wt. % of sodium perborate, 10 wt. % of sodium pyrophosphate, 3 wt. % of a protease, 5 wt. % of sodium dodecylbenzenesulfonate, 10 wt. % of sodium hydrogen carbonate and 12 wt. % of sodium sulfate.

COMPARATIVE EXAMPLE 2

A commercially available cleaning agent for dental spittoon and drainpipes was prepared as the sample of Comparative Example 2. The sample solution contained a lipase, sodium hydrogencarbonate, tartaric acid, sodium hydrogentartrate, sodium carbonate and N-acylamino acid as main components.

Experiments

[Experiment 1]

Calcium phosphate tablets were made, 5 mm in diameter, using a tableting machine.

The 10 tablets of calcium phosphate were placed into 3 of 500 ml beakers, and the experimental solutions of Invention Example 1 and Comparative Examples 1 and 2 were employed, each of 100 ml, into the beakers. Calcium phosphate tablets for alterations in those solution were examined at the room temperature.

[Experiment 2]

Calcium carbonate tablets were made, 5 mm in diameter, using a tableting machine.

Ecperimenal design was the same as Experiment 1 to check the calcium carbonate.

[Experiment 3]

Calcium oxalate tablets were made, 5 mm in diameter, using a tableting machine.

Calcium sulfate tablets were evaluated in the same manner as Experiment 1.

[Experiment 4]

Calcium sulfate tablets were made, 5 mm in diameter, using a tableting machine.

Changing patterns of the calcium sulfate tablets were observed in the same manner as Experiment 1.

Incidentally, with reference to the experiments 1 to 4, calcium phosphate, calcium carbonate, calcium oxalate and calcium sulfate were purchased from Wako Junyaku Co., Ltd. in Japan.

[Experiment 5]

About 100 g of solid plaster of Paris were kept to remain in a drain trap, and 180 ml of the sample solution of Invention Example 1 was passed through the trap. Changes of plaster of Paris were observed. Experiments were conducted also in the samples of Comparative Examples 1 and 2 as the same manner of Invention Example 1 for changes of plaster of Paris.

[Experiment 6]

Three test pieces (approximately 1×1×0.2 cm) of a metal alloy (cobalt, nickel, gold, silver, platinum), widely used for dentures were prepared, exposed to flames for a color change to black, oxidation of metal surface. The test pieces were placed into three 100-ml beakers, respectively, and they were checked for color changes in oxidized film in the sample solutions of Invention Example 1, and Comparative Examples 1 and 2 (each 50 ml).

[Experiment 7]

Dentures with dental plaque and calculus deposited on the surface of dentures were immersed in the sample solutions of Invention Example 1 and Comparative Examples 1, and checked for changes in the deposits. The plaque contains organic substances including fats and proteins, while the calculus contains magnesium compounds in addition to calcium compounds.

[Experiment 8]

About 100 g of human discharges deposited on toilet bowls were given, then immersed in 180 ml of the sample solution of Invention Example 1 and tested for changes.

[Experiment 9]

Four tablets of the sample of Invention Example 2 and four tablets of calcium phosphate prepared in Experiment 1 were placed in a dental spittoon, and water was passed through the spittoon at a rate of 50 ml/min for 1 hour. The tablets of the sample and the calcium phosphate were then checked for the weight loss.

[Experiment 10]

Eight tablets of the sample of Invention Example 2 were placed into each of a vacuum strainer of a dental unit and a spittoon, water was continuously passed through each device at a rate of 50 ml/min, and drainpipes connected to the strainer and the spittoon were checked for changes in the scale (containing calcium compounds and magnesium compounds) deposited on the pipe inner wall.

Experimental Results

Table 1 shows the results of Experiments 1 to 10.

The result of Experiment 6 indicates that the sample solution of Invention Example 1 has an effect to remove the metal oxide film.

With reference to the result of Experiment 7, the sample solution of Invention Example 1 and Comparative Example 1 are comparable in the effect of removing fats and proteins in the dental plaque. Although Invention Example 1 shows an effect to remove calcium compounds as of calculus, Comparative Example 1 was found almost ineffective in this respect. The effect of Invention Example 1 to remove dental plaque is thought attributable to the destruction of various bacteria present in the plaque. The removing agent of the present invention inhibits the growth of plaque, when used for cleaning dentures periodically. The agent of the invention is expected to diminish the formation of dental calculus.

The result of Experiment 8 indicates that Invention Example 1 is effective for decomposing the urine discharges deposited on the toilet bowl. The deposit consists predominantly of organic substances resulting from decomposition with bacteria and calcium deposits. This indicates that the sample solution of Invention Example 1 has an effect to exclude such soiled materials.

Experiment 9 shows that the sample solution of Invention Example 2 containing a binder dissolved in water as delayed, indicating that only the dissolved portion contributed to the removal of calcium phosphate.

The result of Experiment 10 reveals that the sample solution of Invention Example 2 was gradually dissolved with water, gradually removing the scale (containing calcium compounds and magnesium compounds) deposited on the drainpipe inner wall.

The removing agent of the present invention is recognized to capable of dissolving calcium compounds almost completely (see Experiments 1 to 5).

Thus, the removing agent of the present invention is effective for dissolving not only calcium compounds but

TABLE 1

|  | Invention Example 1 | Invention Example 2 | Comparative Example 1 | Comparative Example 2 |
| --- | --- | --- | --- | --- |
| Exp. 1 | Almost changed to powder in 30 min. Wholly dissolved in about 3 hrs. | — | Almost no change | Almost no change |
| Exp. 2 | Almost changed to powder in 30 min. Wholly dissolved in about 3 hrs. | — | Almost no change | Almost no change |
| Exp. 3 | Almost changed to powder in 30 min. Wholly dissolved in about 3 hrs. | — | Almost no change | Almost no change |
| Exp. 4 | Almost changed to powder in 30 min. Wholly dissolved in about 3 hrs. | — | Almost no change | Almost no change |
| Exp. 5 | Wholly changed to powder in about 1 hr. | — | Almost no change | Almost no change |
| Exp. 6 | Oxide film disappeared in 5 min, revealing metallic brilliant. | — | Almost no change | Almost no change |
| Exp. 7 | Plaque (fat, proteins and organic substances) and calculus (Ca compounds, etc.) were removed in about 1 hr. | — | Plaque (fat, proteins and organic substances) was removed in about 1 hr, but calculus (Ca compounds, etc.) remained almost unremoved. | — |
| Exp. 8 | Deposit almost dissolved in 20 min | — | — | — |
| Exp. 9 | — | 1.3% weight loss in invention tablets. 18% weight loss in calcium phosphate tables. | — | — |
| Exp. 10 | — | Scale deposit was removed in 1 day. | — | — |

The results of Experiments 1 to 5 reveal that the sample solution of Invention Example 1 is effective for removing various calcium compounds, but that the sample solutions of Comparative Examples 1 and 2 are almost ineffective for removing calcium compounds.

also magnesium compounds (see Experiments 7 and 10) because both calcium and magnesium are elements included in alkaline earth metals and similar in chemical properties.

The removing agent of the present invention characteristically consists of compounds with highly biodegradable and is excellent in amenability to environments and therefore suitable for excluding solid materials in the inner wall of the drainpipes including those for dental unit, toilet drainpipes, drainpipes in operating rooms and supply rooms of hospitals, and drainpipes in trains, vessels, aircraft and like transporation means, and also for removing filthy adhesives in various apparatus in the field of chemical industry power generator equipment, heat exchangers and so on, which are associated with calcium and mineralized deposits.

The agent of the invention for removing calcium compounds and the like also acts to destroy organic substances produced by bacteria, is therefore capable of effectively removing both plaque and calculus, and is more advantageous to use as a denture cleaning agent than conventional agents.

For removing dental calculus containing calcium compounds firmly deposited on the walls of drainpipes, it was conventionally used with a strong acid solution which is some difficult to handle in the safety use or which possibly occurs erosion or corrosion to metals of the drain pipes, whereas the removing agent of the present invention is adequately usable with safety and without metal corrosion.

The agent of the present invention has also activity to dissolve organic substances including fats and proteins and is therefore suitable for use as an agent for removing deposits or accumulations of such organic substances in drain pipes.

The removing agent of the invention also has an effect to remove metal oxide films and is suitable for use as a cleaning agent for various drainpipes.

The embodiment described above is intended to illustrate the present invention and should not be construed as limiting the invention set forth in the appended claims. It should be understood that various modifications can be made within the scope of the claims.

What is claimed is:

1. A removing agent for use in removing calcium compounds and/or magnesium compounds deposited on an article, the removing agent consisting essentially of malic acid and citric acid as a hydroxycarboxylic acid and a sulfamic acid, wherein the hydroxycarboxylic acid and the sulfamic acid are used in a ratio by weight of approximately 1:9 to 7:3; and wherein the sulfamic acid is amidosulfamic acid, N-alkyl and N-aryl derivatives of the amidosulfamic acid.

2. A removing agent for use in removing calcium compounds and/or magnesium compounds deposited on an article, the removing agent prepared by mixing 5 to 100 parts by weight of a binder with 100 parts by weight of the base composition consisting essentially of malic acid and citric acid as a hydroxycarboxylic acid and a sulfamic acid, and shaping the resulting mixture, wherein the hydroxycarboxylic acid and the sulfamic acid are used in a ratio of approximately 1:9 to 7:3; and wherein the sulfamic acid is amidosulfamic acid, N-alkyl and N-aryl derivatives of the amidosulfamic acid.

3. The removing agent according to claim 2, wherein said binder is selected from carboxymethyl-cellulose (CMC), sodium carboxymethylcellulose (CMC-Na), polyvinyl pyrrolidone (PVP), hydroxypropyl cellulose (HPC), hydroxypropyl methylcellulose (HPMC), methylcellulose (MC), hydroxypropyl starch (HPS), and similar carbohydrates and organic polysaccharide.

* * * * *